United States Patent [19]

Chikashige

[11] 4,412,531

[45] Nov. 1, 1983

[54] SUCTION DEVICE FOR ENDOSCOPE

[75] Inventor: Kiyoshi Chikashige, Kawagoe, Japan

[73] Assignee: Kabushiki Kaisha Medos Kenkyusho, Kawagoe, Japan

[21] Appl. No.: 194,701

[22] Filed: Oct. 6, 1980

[30] Foreign Application Priority Data

Oct. 6, 1979 [JP] Japan .......................... 54-138814[U]

[51] Int. Cl.$^3$ .............................................. A61B 1/00
[52] U.S. Cl. ...................................................... 128/4
[58] Field of Search ........................................ 128/4–5, 128/766, 274, 767, 277, 677, 685, 6; 137/625.26

[56] References Cited

U.S. PATENT DOCUMENTS

| 1,527,872 | 2/1925 | Herrick | 128/274 |
| 2,638,108 | 5/1953 | Williams et al. | 137/625.26 |
| 3,608,584 | 9/1971 | Vaughn | 137/625.26 |
| 3,678,959 | 7/1972 | Liposky | 128/274 |
| 3,726,272 | 4/1973 | Fukami et al. | 128/6 |
| 3,958,566 | 5/1976 | Farihata | 128/274 |

FOREIGN PATENT DOCUMENTS 2249905 4/1974 Fed. Rep. of Germany ......................... 137/625.26

Primary Examiner—William E. Kamm
Assistant Examiner—Max F. Hindenburg
Attorney, Agent, or Firm—Sughrue, Mion, Zinn, Macpeak and Seas

[57] ABSTRACT

A suction device for an endoscope in which there is no need for the operator to close a suction pipe with his finger and in which cleaning and sterilizing are readily implemented. A suction path extends from a forceps insertion hole in a forceps receiver. A plug assembly is detachably inserted in the suction path in close contact therewith. The plug assembly includes a piston at least a portion of which is made of an elastic material and a cylinder member into which the piston is loosely fitted. The cylinder member has valve seats formed at first and second ends thereof while the piston is furnished with corresponding first and second abutting portions. An elastic extended member biases the piston outwardly. A suction hole is formed in the cylinder member through which suction pressure is communicated.

10 Claims, 6 Drawing Figures

SUCTION DEVICE FOR ENDOSCOPE

BACKGROUND OF THE INVENTION

The present invention relates to a suction device for an endoscope which is used to remove mucus or undesired matter from a body cavity to be examined.

It is difficult to adequately observe a region of a body cavity to be examined with an endoscope if the region is covered with mucus or other undesired matter. The lens window at the top of the endoscope inserted into the body cavity often tends to collect moisture making it necessary to deliver cleaning water to the lens window to clean the window. It is necessary to suck away and remove the mucus or cleaning water as required.

For this purpose, heretofore endoscopes have been provided with a forceps insertion pipe with which mucus is removed by a suction pipe which branches at the manual operation unit of the endoscope from the forceps insertion pipe. More specifically, to operate such a device the operator's finger is placed over an opening which protrudes from the suction pipe operating unit body to prevent external air from flowing into the suction pipe. At this time, the pressure in the suction pipe is decreased by a suction pump coupled to the suction pipe thereby to suck and remove the mucus or the like through the forceps insertion pipe from the body cavity.

However, this technique is disadvantageous in the following points. The liquid removed by the conventional endoscope may stick directly to the operator's finger which was used to close the protruding opening of the suction pipe. A finger thus contaminated may touch the operation unit of the endoscope or bioptic instruments such as the forceps used in observing the desired region of the body cavity, other medical instruments, an endoscope camera, or peripheral equipment as a result of which bacteria may be dispersed. Especially for the examination of a patient with an infectious disease, it is impossible to maintain the sterile condition of all the equipment touched by the finger and accordingly the surrounding equipment becomes contaminated by bacteria.

During a suction operation with the operator's finger closing the aforementioned opening, the liquid to be removed is being moved at a high speed by strong suction pressure from the end portion of the endoscope. When the finger is removed from the opening of the suction pipe to suspend the suction operation, the sucked liquid tends to splash through the outlet of the forceps receiver or the end of the suction pipe over the operation unit of the endoscope. This is considerably unsanitary.

Furthermore, the suction operation control unit has a necessarily intricate configuration and therefore it is difficult to clean the inner wall of the suction pipe and the operation unit of the removed liquid. In addition, the suction operation is carried out through cylindrical members which telescope and the junctions between the cylindrical members tend to hold waste matter.

Accordingly, an object of the invention is to provide a suction device for an endoscope in which the arrangement of a suction operation unit is such that the need for directly closing the suction pipe with a finger is eliminated and cleaning and sterilizing can be readily achieved.

SUMMARY OF THE INVENTION

These, as well as other objects of the invention, are met by a suction device for an endoscope which has a forceps receiver including a forceps insertion bore. A suction path is constructed so as to extend radially outward from the forceps insertion bore and a plug assembly is detachably inserted in the suction path in close contact with the suction path. The plug assembly includes a piston at least one portion of which is made of elastic material and a cylinder member into which the piston is loosely fitted. The cylinder member has valve seats formed at first and second portions thereof while the piston has first and second abutting portions which conform to the respective first and second valve seats. The piston further has an elastic extended member extending from the portion made of elastic material. The extended member has an end portion abutting against a stationary portion of the suction device such that the extended member biases the piston to move upwardly. The cylinder member is provided with a suction hole at a position between the two valve seats, the suction hole being adapted to be coupled to a suction pump.

In a preferred embodiment, the piston has an elastic end portion having a slit adapted to clamp a forceps operating flexible guide pipe and in which, when the piston is depressed, the elastic end portion protrudes into the forceps insertion bore so as to close the insertion bore. In another preferred embodiment, an elastic tube covers the inner wall of the forceps insertion bore around a position from which the suction path extends. In this embodiment, when the piston is depressed, the elastic tube is collapsed by the piston thus closing the forceps insertion bore.

A tightening ring may be used to secure the cylinder member to the means which forms the suction path. A hole may be provided in the extended portion which may be elastic and have a semi-spherical shape and may be formed integrally with the piston.

DESCRIPTION OF THE PREFERRED EMBODIMENTS

The present invention will be described with reference to the accompanying drawings.

Figure 1:
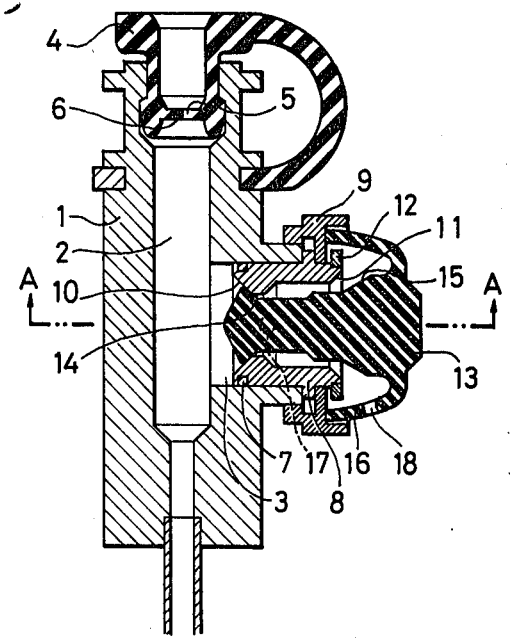
FIG. 1 is a longitudinal sectional view showing a first embodiment of a suction device constructed according to the invention.
Figure 2:
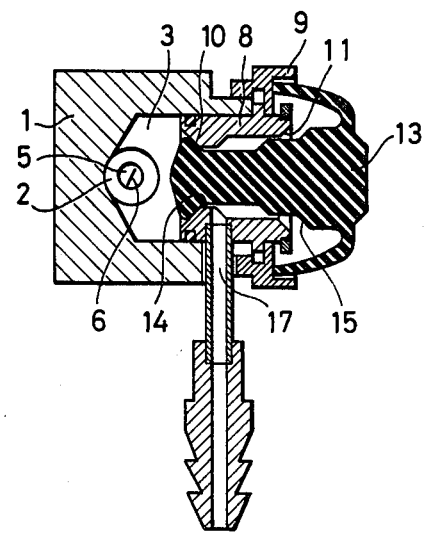
FIG. 2 is a sectional view taken along line A—A in FIG. 1.
Figure 3:
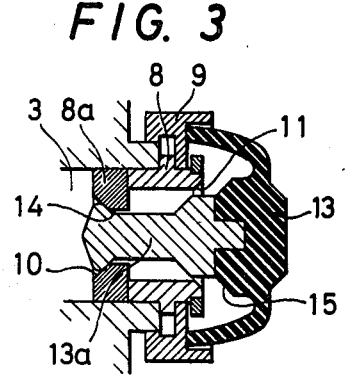
FIG. 3 is a longitudinal sectional view of a second embodiment of a suction device constructed according to the invention.

FIG. 1 is a longitudinal sectional view showing a preferred embodiment of a suction device for an endoscope constructed according to the invention and FIG. 2 is a sectional view taken along line A—A in FIG. 1. A forceps receiver body 1 is integrally or substantially integrally coupled to the manual operation unit of the endoscope. The body 1 has a forceps insertion bore 2 and a suction path 3 which extends radially outward from the forceps insertion bore 2 perpendicularly to the axis of the forceps insertion bore 2. The suction path 3 extends to a container for housing mucus and other undesired matter removed from a body cavity. The outer end opening of the forceps insertion bore 2 is closed by a plug 4 made of an elastic mateial such as rubber which is detachably inserted into the insertion bore 2 under pressure. The plug 4 has a central web in which a groove 6 is cut so that forceps can be inserted into the forceps insertion bore 2 through the groove 6 of the plug 4 inserted into the outer end opening under pressure. When either the forceps is inserted or is not inserted into the forceps insertion bore, the outer end opening of the forceps insertion bore is maintained closed because the cut groove 6 tends to close itself because of the elasticity of the material of the central film 5.

In the suction path 3 is inserted a cylinder 8 on the outer wall of which an O-ring 7 is provided so that the cylinder 8 is in close engagement with the suction path 3. The cylinder 8 is inserted under pressure into the suction path 3 by means of a tightening ring 9. The cylinder 8 has two end faces. The end face closer to the forceps insertion bore is tapered to form a first valve seat 10 and the remaining outer end face is also tapered to form a second valve seat 11. External air is introduced through the outer end portion of the cylinder 8. A ring 12 is secured on the outer end portion of the cylinder 8 so that the cylinder 8 is detained by the tightening ring 9.

A plug-shaped piston 13 is provided which is made of an elastic material such as rubber. The piston 13 has an inner end portion which is shaped such that its inner surface is sloped so as to conform to the configuration of the valve seat 10 thus forming a first abutting portion 14 and a middle portion in succession from the inner end portion with the middle portion being smaller in diameter than the other portions. The piston 13 further has an outer end portion which is shaped such that the inner surface thereof slopes in conformance with the configuration of the valve seat 11 thus serving as a second abutting portion 15. The outer edge of the piston 13 is curved to form a semispherical elastic extended member 16 the outer edge of which abuts against the flange of the tightening ring 9. The piston 13 constructed as described above is mounted in the cylinder 8 of the suction path 3 in such a manner that its inner expanded portion is inserted into the cylinder by being pushed over the valve seat 10. In the inserted position, the piston 13 is biased to move outwardly by the elasticity of the semispherical portion 16 abutting against the flange of the tightening ring 9 with the valve seat 10 in close contact with the abutting portion 14.

A suction hole 17 is provided in the cylinder 8 of the suction path 3 between the valve seats 10 and 11. The outer end opening of the suction hole 17 is connected to a suction pump provided separately.

The suction path 3 and the outer end portion of the cylinder 8 are covered by the semi-spherical portion 16 of the piston 13 through the tightening ring 9 and an outer end opening 18 is formed in the portion 16 for introducing external air. The outer end opening 18 may be replaced by any other means capable of introducing external air into the suction path 3. For instance, the opening 18 may be formed in the tightening ring 9.

In the above-described example, the piston 13 is made of elastic material. However, in a second embodiment the piston 13 may be so modified that the portion of the piston disposed in the cylinder 8 is a hard portion 13a made of metal or synthetic resin while the remaining head and semi-spherical portion 16 are integrally made of an elastic material. In this case, it is necessary to provide an elastic ring 8a which is not integral with the cylinder 8 as the valve seat 10 for the abutting portion 14 of the hard portion 13a.

The above-described example of a suction device constructed according to the invention may be used after the suction plug composed of the cylinder 8 and the piston 13 has been fixedly secured to the suction path 3 with the tightening ring 9. During the use of the suction device, the groove 6 cut in the central web of the plug 4 tends to close itself because of the elastic force of the material of the web. Thus the forceps insertion bore is maintained closed whether or not the forceps has been inserted thereinto and the piston 13 is maintained pushed outwardly by the elastic force of the semi-spherical portion 16 as shown in FIG. 1. When the suction pump is operated, the suction pressure is applied through the suction hole 17. The suction operation does not affect the forceps insertion bore 2 which has been closed by the abutting portion 14 in close contact with the valve seat 10 but allows external air to flow in through the outer end opening 18 of the cylinder 8 which is opened by the abutting portion 15 which is lifted from its seat 11. Thus, under this condition, no negative pressure is created in the cylinder and no overload is applied to the suction pump.

When it is required to suck mucus or the like out of a body cavity, the piston 13 is depressed by the operator's finger against the elastic force provided by the semispherical portion thereby causing the abutting portion 14 to move away from the seat 10. As a result, the suction force is applied to the forceps insertion bore 2 to cause the suction of mucus from the body cavity. During the depression of the piston, a state may occur in which the path leading to the forceps insertion bore is opened and the external air introducing path is not completely closed. Even in this state, the gap, or the external air introducing path, between the piston 13 and the cylinder 8 is small and therefore the sucked liquid will not splash out through the gap.

When the piston 13 is strongly depressed to cause the abutting portion 15 to form a tight seal against the seat 11, the introduction of the external air is suspended at which time the suction operation can be carried out. The suction force can be controlled as required by adjusting the depression of the piston 13.

In the above-described embodiment, the inserting opening of the forceps insertion bore 2 is closed with the plug 4, which is provided as a separate component, to perform the suction operation. In the third embodiment of the suction device of the invention described below, the suction operation can be carried out without using such a plug.

Figure 4:
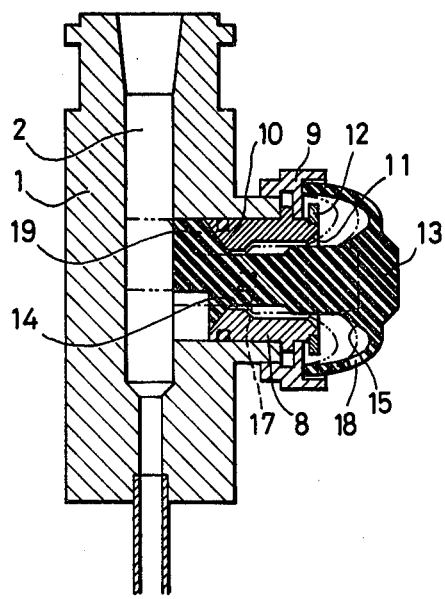
FIGS. 4 and 5 are a longitudinal sectional view showing a third embodiment of a suction device according to the invention and a perspective view showing specific components of the device of FIG. 4, respectively.
Figure 5:
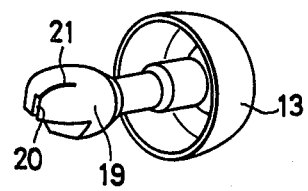

FIG. 4 is a longitudinal sectional view of the third embodiment of the suction device and FIG. 5 is a perspective view of a piston 13 used in the suction device of FIG. 4. In FIGS. 4 and 5, those components which have been described with reference to FIGS. 1 and 2 are similarly numbered.

In this embodiment, the expanded end portion of the piston 13 is further extended so that, when the piston 13 is depressed, the end portion 19 enters the forceps insertion bore 2 perpendicularly to the axis of the insertion bore 2, indicated by the dotted line in FIG. 4, so as to close the bore 2. A receiving groove 20 is cut in the central portion of the end face of the expanded end portion 19 and a slot 21 is formed leading away from the receiving groove 20.

In the case where no forceps is inserted into the forceps insertion bore 2, the end portion 19 will abut against the wall of the forceps insertion bore 2 upon depressing the piston 13 as a result of which the end portion 19 is brought into close contact with the wall of the forceps insertion bore 2 with the receiving groove 20 collapsed to close the forceps insertion bore 2. In the case where a forceps is inserted in the forceps insertion bore 2, when the piston 13 is depressed, a forceps operating flexible pipe is clamped by the receiving groove 20 of the end portion 19. When the piston 13 is further depressed, the flexible pipe is clamped by the slit 21 as a result of which the end portion 19 is brought into close contact with the outer wall of the flexible pipe and the wall of the forceps insertion bore 2 to close the bore 2. With the forceps insertion bore 2 thus closed, a suction operation is carried out by operating the piston 13 as in the first embodiment described above.

Figure 6:
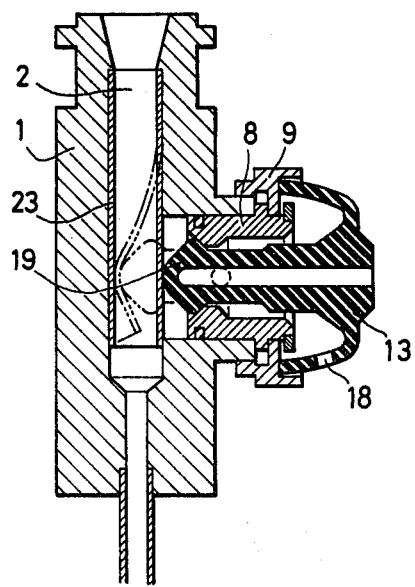
FIG. 6 is a longitudinal sectional view showing a fourth embodiment of a suction device of the invention.

A further embodiment of a suction device constructed according to the invention is shown in FIG. 6 which is a longitudinal sectional view. In this embodiment also, the forceps insertion bore 2 is closed by a piston 13. A flexible tube 23 is provided around the position in the forceps insertion bore from which the suction path extends outwardly so that the outer wall of the flexible tube 23 can be depressed with the end portion 19 of the piston 13. When the end portion 19 of the piston 13 depresses the outer wall of the flexible tube 23, the tube 23 collapses, as indicated by the dotted line in FIG. 6, thus closing the forceps insertion bore 2.

The elasticity of the end portion 19 of the piston 13 must be such that the end portion 19 is harder than the flexible tube 23. In addition, the end portion 19 must have a sufficiently low elasticity that, if the forceps insertion bore is closed with the flexible tube 23 slightly deformed, for instance, during the insertion of a forceps, the end portion 19 is collapsible to permit movement of the piston 13. This requirement may be achieved, that is, the elasticity of the end portion can be controlled, by suitably selecting a material for fabricating the piston 13, by modifying the piston 13 to have a hollow form, by forming a hollow region only in the end portion 19 of the piston, or by shaping the end portion 19 to have another configuration which achieves this requirement.

In cleaning and sterilizing the above-described devices according to the above described embodiments of the invention, first the tightening ring 9 is loosened. Then, the suction plug composed of the ring 9 is loosened. Then, the suction hole 17 can be readily removed from the suction path 3. The piston 13 can be removed from the cylinder 8 by pulling hard on the piston 13. These components thus disassembled can be cleaned and sterilized in a sterilizing solution. The suction path 3 can be readily cleaned with a brush.

As is clear from the above description, in the suction device according to the invention, the plug assembly in the form of a piston is inserted into the suction path branching from the forceps insertion bore to control the operation of sucking mucus or the like out of a body cavity. With the structure of the invention, the operator's fingers are protected from contamination by liquid sucked, and splashing of sucked liquid through the opening of the suction path is prevented when the forceps insertion bore is closed for suction. Furthermore, the components can be readily cleaned and sterilized.

The suction device according to the invention uses no components such as elastic springs to which sucked liquid sticks readily and uses a plug assembly which can be manufactured at low cost by integral molding or the like. Therefore, the suction device of the invention has a low manufacturing cost. When the plug assembly is worn out, it can be readily replaced by a new one thus resulting in inexpensive and effective maintenance of the suction device.

What is claimed is:

1. A suction device for an endoscope, the endoscope having a forceps receiver which has a closable forceps insertion bore therein, comprising:
   means for forming a suction path extending from said forceps insetion bore; and
   a plug assembly detachably inserted in said suction path in close contact with said suction path forming means, said plug assembly comprising: a ring, a piston, at least one portion of which is made of a deformable material; and a cylinder member into which said piston is slidably fitted, said cylinder member having valve seats formed at first and second portions thereof, said piston having first and second abutting portions for alternatively engaging said first and second valve seats, wherein abutment with the first valve seat allows passage of ambient air into said bore and wherein abutment with the second valve seat allows for suction in said bore said piston further having an elastic extended member extending outwardly away from said forceps insertion bore from said portion made of said elastic material, said extended member having an end portion abutting against said ring, said extended member biasing said piston so that said piston tends to move outwardly away from said forceps insertion bore, said cylinder member being provided with a suction hole; and
   a suction pump coupled to said suction hole.

2. The suction device as claimed in claim 1 in which said piston has an elastic end portion which has a groove adapted to clamp a forceps operating flexible guide pipe and in which, when said piston is depressed, said elastic end portion protrudes into said forceps insertion bore to close said forceps insertion bore.

3. The suction device as claimed in claim 1 further comprising: an elastic tube covering the inner wall of said forceps insertion bore around a position from which said suction path extends whereby, when said piston is depressed, said elastic tube is collapsed by said piston thus closing said forceps insertion bore.

4. The suction device as claimed in claim 1 wherein said ring comprises a tightening ring for securing said cylinder member to said suction path forming means.

5. The suction device as claimed in claim 1 further comprising an O-ring for sealing said cylinder member to said suction path.

6. The suction device as claimed in claim 1 wherein said elastic extended member has a semi-spherical shape.

7. The suction device as claimed in claim 1 wherein said elastic extended member has a hole therein.

8. The suction device as claimed in claim 1 wherein said elastic extended member and said piston comprise a single element.

9. The suction device as claimed in claim 1 wherein said first abutting portion of said piston is made of a hard material.

10. The suction device as claimed in claim 3 wherein said piston has a hollow center portion.

* * * * *